United States Patent [19]

Hargadon

[11] 4,261,348

[45] Apr. 14, 1981

[54] APPENDAGE CASTING SUPPORT STAND

[76] Inventor: Charles M. Hargadon, 6107 Orion Rd., Louisville, Ky. 40222

[21] Appl. No.: 83,903

[22] Filed: Oct. 11, 1979

[51] Int. Cl.[3] ............................................. A61F 5/04
[52] U.S. Cl. .................................................... 128/83
[58] Field of Search ................................... 128/83, 82

[56] References Cited

U.S. PATENT DOCUMENTS

| | | | |
|---|---|---|---|
| 1,266,367 | 5/1918 | Wilson .................................... | 128/83 |
| 1,516,795 | 11/1924 | Schwarting ....................... | 128/83 X |
| 2,119,325 | 5/1938 | Goodhart ........................... | 128/83 X |
| 2,376,507 | 5/1945 | Ruther .............................. | 128/83 X |
| 3,908,643 | 9/1975 | Bliss .................................... | 128/83 |

FOREIGN PATENT DOCUMENTS 147865  1/1904  Fed. Rep. of Germany ............. 128/83

*Primary Examiner*—John D. Yasko
*Attorney, Agent, or Firm*—Leitner, Palan, Martin & Bernstein

[57] ABSTRACT

A support stand including a base and a thin platform extending cantilevered from the base. The height and angle of the platform is adjustable. The platform is flexible spring steel to accommodate the appendage to be cast and is readily removed by sliding it out of the completed cast.

2 Claims, 3 Drawing Figures

U.S. Patent  Apr. 14, 1981  Sheet 1 of 2  4,261,348

APPENDAGE CASTING SUPPORT STAND

BACKGROUND OF THE INVENTION

The present invention relates generally to support stands and more specifically to a stand to support an appendage which is being cast.

The casting of an appendage generally includes wrapping the appendage with a bandage or gauze-type material, for example, Webril, to enclose the area to be cast so as to protect the skin, applying the casting material, for example, plaster around the wrapped appendage, and allowing the cast to dry or set. Where the appendage to be cast is a foot, leg, or an ankle, it must be free of all obstructions to allow the casting operation. Techniques to support the appendage while casting have required an assistant to either hold the extremity in the proper alignment in a somewhat uncomfortable position or for the physician or technician to support the extremity on their knee. This generally increases the discomfort of the patient in addition to that of injury to the appendage to be cast.

Thus, there exists a need for a support stand for an appendage to be cast which will accomodate the appendage and relieve the patient of any additional discomfort.

SUMMARY OF THE INVENTION

An object of the present invention is to provide a stand to support an appendage to be cast.

Another object of the present invention is to provide a stand or support means for an appendage to be cast which will not cause any additional discomfort to the patient.

A further object of the invention is to provide a stand which will support the appendage to be cast which is adjustable to accomodate appendage.

These and other objects of the invention are attained by providing a support stand having a thin resilient platform cantilevered from a base to accomodate the appendage to be cast. The stand allows for the adjustment of the height and the angle from the horizontal of the thin platform. By forming the platform of spring steel, it will flex with the weight of the appendage to accomodate it. The height adjustment is accomplished by two telescoping members with a means to lock the telescopic members to a specific height. The horizontal angular adjustment includes a vertical projection of the platform being pivotally received in a forked portion of the base and having a locking means therefore. The base extends a greater horizontal distance in the direction of the cantilever platform than in any other directions to provide stability for the stand.

Objects, advantages and novel features of the present invention will become apparent from the following detailed description of the invention when considered in conjunction with the accompanying drawings.

DESCRIPTION OF THE PREFERRED EMBODIMENTS

Figure 1:
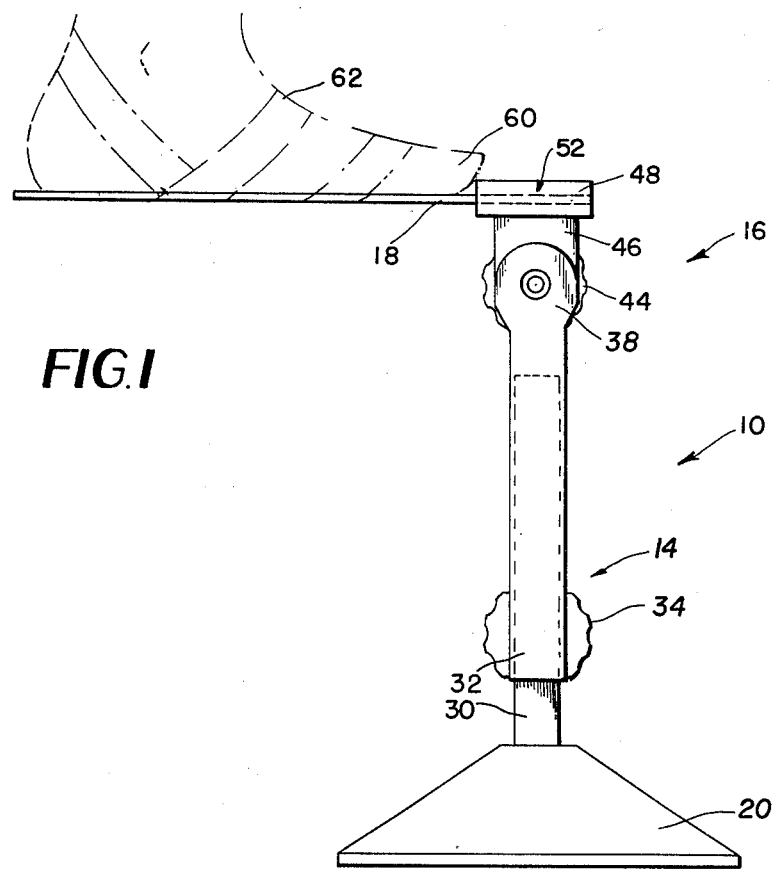
FIG. 1 is a side elevational view of a support stand incorporating the principles of the present invention.
Figure 2:
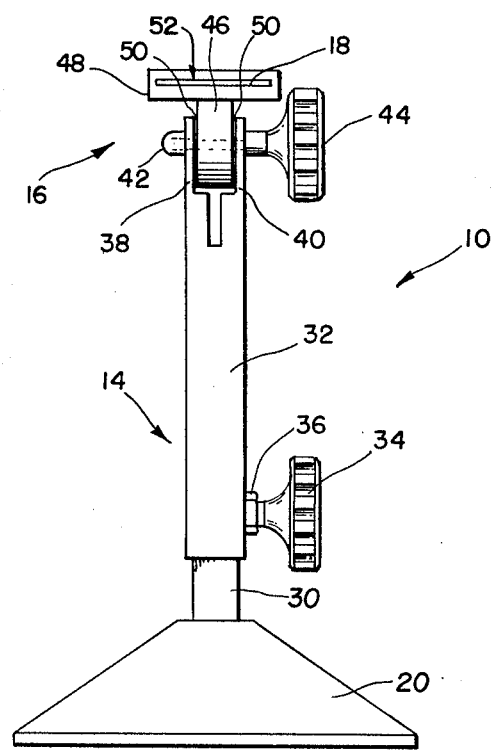
FIG. 2 is a front elevational view of a support stand incorporating the principles of the present invention.
Figure 3:
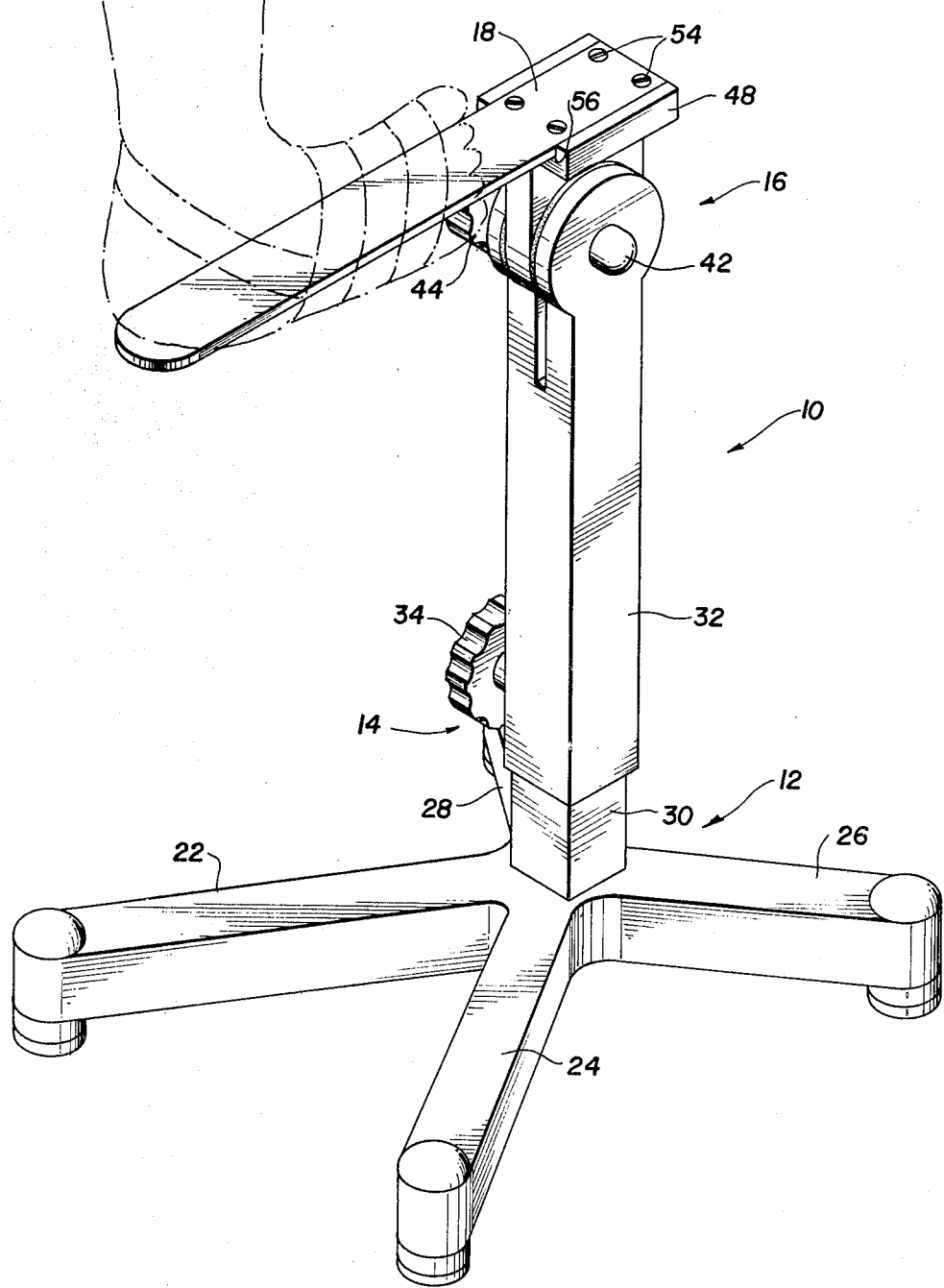
FIG. 3 is a perspective of another support stand incorporating the principles of the present invention.

As illustrated in FIGS. 1 through 3, the support stand 10 includes a base 12, a height adjustment section 14, an angular adjustment section 16 and a platform 18. The base 12, as illustrated in FIGS. 1 and 2, may be a weighted element 20 or may include a plurality of legs 22, 24, 26, and 29, as illustrated in FIG. 3. Since the weight of the appendage will be resting upon the platform 18 which is a cantilevered extension, it is preferred to use the four-legged configuration of FIG. 3. It should be noted that legs 22 and 24 extend substantially further in horizontal direction than legs 26 and 28. This horizontal direction is in the direction of the cantilever extension of 18 and provides the necessary stability for the stand. Alternatively, the weighted horizontal base may be rectangular and extend in a greater horizontal direction in the extended cantilever direction of the platform 18 to provide the function of the four-legged construction of FIG. 3. The base 12 rests directly on the floor or other support surface and may include pads on the bottom thereof or may include casters or other appropriate rollers.

The height adjustment section 14 includes a post 30 secured to and extending vertically from the base 20 and a sleeve 32 which telescopically receives the post 30. A locking device 34 for example a threaded element, traverses a threaded lug 36 mounted on the sleeve 32 to engage the exterior surface of post 30. The post 30 may include a plurality of openings to receive the threaded lock 34 to lock the sleeve 32 at a plurality of fixed or preselected locations or heights. As an expedient, the surface of post 30 is smooth such that the sleeve 32 may be positioned in any desired height. Although a simple threaded lock 34 has been shown, more sophisticated mechanism may be used to adjust the height of sleeve 32 relative to post 30. For example, a lateral face of post 30 may include horizontal grooves or teeth and the lock 34 may include a screw or teeth to ride over teeth or horizontal grooves of post 30 so as to transport the sleeve 32 up and down the post 30 by rotation of the handle of lock 34. The illustrated lock 34 is mechanically simple and consequently is more inexpensively to produce.

The horizontal angular adjustment section 16 includes opposed ears 38 and 40 which are a forked termination of sleeve 32. A threaded lug or nut 42 is mounted to ear 38 and receives a threaded element or screw 44. The other portion of the angular adjustment section 16 includes a projection 46 extending vertically from horizontal securement portion 48. The projection 46 rests in the fork between ears 38 and 40 and has an aperture to permit the shaft of screw 44 to traverse therethrough and to pivotally mount the projection 46 and horizontal portion 48 thereto. A pair of washers 50 are positioned between the projection 46 and the forked ears 38 and 40. The horizontal angular position of the platform 18 is adjusted by loosening the lock 44 and rotating the horizontal platform 18 and projection 46 until the desired angular position of the platform 18 is achieved. Lock 44 is then threaded into threaded lug 42 tightening the ears 38 and 40 of the forked portion to clamp or lock the projection 46 there between.

It should be noted that although the projection 46 and the interior surface of ears 38 and 40 are shown as smooth and are used with washers, other types of surfaces may be used to form a tight lock there between. For example, the sides of projection 46 and the interior surface of ears 38 and 40 may have mating serrated surfaces which will add a positive lock against rotation, in addition to that applied by the pressure of the locking member 44.

The platform 18, which is preferrably a flexible material, for example, spring steel, may be slid into a closed channel 52 in horizontal element 48 as illustrated in FIGS. 1 and 2 or secured by fasteners 54 in an open channel 56 in the top surface of horizontal element 48. Although the open channel with fasteners securement of FIG. 3 is preferred, the closed channel-sliding engagement of FIGS. 1 and 2 may also be used.

The significance of the structure will become apparent from the description of the method of casting an appendage using such structure. For purposes of example, the foot will be selected as the appendage to be cast. It should be noted that other appendages may be cast, for example, legs or ankles. To cast a leg, ankle or foot, the patient will generally be positioned on an examining table or other surface such that the foot dangles therefrom above the floor. The support stand 10 is then positioned under the foot using the height adjustment 14 and the angular adjustment 16 such that the foot is supported comfortably on the platform 18. The flexible steel 18 will flex about a horizontal axis to accomodate the weight of the foot comfortably. It should be noted that the width of the platform 18 is selected to be smaller than the width of the foot. With the foot so supported and held steady, the foot and platform are bound with a bandage type material, for example, Webril, over the area to be cast. As illustrated in FIG. 1, the foot 60 and the platform are both bound by the Webril 62. The wrapped appendage is then covered with casting material. Once the casting material has dried or set, the platform 18 is removed by sliding it from the cast. For the support stand of FIG. 3, the hole support stand is moved horizontally away from the appendage. For the support stand of FIGS. 1 and 2, the total supports may be moved or the platform 18 may be removed by sliding it from the cast as well as channel 52 of the stand 10.

From the preceding description of the preferred embodiments, it is evident that the objects of the invention are attained and that a support stand is provided which will support appendages to be cast in a comfortable manner and steady it during casting. Although the invention has been described and illustrated in detailed, it is to be clearly understood that the same is by way of illustration and example only and is not to be taken by way of limitation. The spirit and scope of this invention are to be limited by the terms of the appended claims.

What is claimed:

1. An appendage casting support comprising:
   base means;
   height adjustment means including a post secured to and extending vertically from said base means;
   a sleeve means for telescopically receiving said post and locking means for locking said sleeve means at any one of a plurality of preselected positions;
   horizontal angular adjustment means including a forked member extending from the top of said sleeve means of said height adjustment means for receiving a projection means pivotally mounted in the groove of said forked member;
   position locking means for locking said projection and said forked member at various angular positions relative to each other;
   horizontal extending means attached to said projection means and having a channel, said channel being open at one end and closed at the other end;
   platform means slidingly received in said channel for easy removal from said channel whereby said platform means is prevented from rotating in a horizontal plane with respect to said base means and said height adjustment means but can be rotated in a vertical plane and locked at various angles to said height adjustment means.

2. An appendage casting support comprising:
   base means;
   height adjustment means including a post secured to and extending vertically from said base means, a sleeve means for telescopically receiving said post and locking means for locking said sleeve means at any one of a plurality of preselected positions;
   horizontal angular adjustment means including a forked member extending from the top of said sleeve means of said height adjustment means for receiving a projection means pivotally mounted in the groove of said forked member;
   position locking means for locking said projection and said forked member at various angular positions relative to each other;
   horizontal extending means attached to said projection means and having a channel, said channel being open at the top and at one end;
   platform means removeably fastened in said channel whereby said platform means is prevented from rotating in a horizontal plane with respect to said base means and said height adjustment means but can be rotated in a vertical plane and locked at various angles to said height adjustment means.

* * * * *